United States Patent [19]

Alferness

[11] Patent Number: 4,915,656
[45] Date of Patent: Apr. 10, 1990

[54] DISCRIMINATING MEDICAL ELECTRODE CONNECTOR

[75] Inventor: Clifton A. Alferness, Woodinville, Wash.

[73] Assignee: Physio-Control Corporation, Redmond, Wash.

[21] Appl. No.: 260,798

[22] Filed: Oct. 21, 1988

[51] Int. Cl.⁴ .......................... H01R 4/48; A61B 5/04
[52] U.S. Cl. ................................ 439/729; 128/639; 128/798; 439/838; 439/909
[58] Field of Search ............... 439/909, 217, 218, 269, 439/296, 725, 729, 819, 822, 829; 128/639, 641, 798, 802, 803

[56] References Cited

U.S. PATENT DOCUMENTS

| | | | |
|---|---|---|---|
| 4,555,155 | 11/1985 | Drake | 439/838 |
| 4,612,936 | 9/1986 | Yamaguchi | 128/802 X |
| 4,702,256 | 10/1987 | Robinson et al. | 439/729 X |
| 4,797,125 | 1/1989 | Malana | 128/639 X |

*Primary Examiner*—William Briggs
*Attorney, Agent, or Firm*—Christensen, O'Connor, Johnson & Kindness

[57] ABSTRACT

A discriminating connector (38) can be connected to a defibrillation electrode (36), but not to an ECG monitoring electrode (10), even though both electrodes (38 and 10) have identical conducting posts (50 and 12). The discriminating connector (38) is formed by upper and lower members (40 and 42) and a pivot (44) that connects the upper and lower members (40 and 42) so as to define an opening (43). A mating receptacle (48) is disposed within an upper wall (74) of the opening (43). A distance (49) between the mating receptacle (48) and the pivot (44) is equal to or greater than a distance (59) between the conducting post (50) and an outer edge (53) of the defibrillation electrode (36) so as to permit the conducting post (50) to be received by the mating receptacle (48). A conductive receptacle (15) in a prior art ECG connector (11) is identical to the mating receptacle (48) and can be attached to the conducting post (50) on the defibrillation electrode (36). The distance (49) of the discriminating connector (38) is less than a distance (19) between the conducting post (12) and an outer edge (30) of the ECG monitoring electrode (10). As a result, the discriminating connector (38) cannot be connected to the ECG monitoring electrode (10).

11 Claims, 4 Drawing Sheets

DISCRIMINATING MEDICAL ELECTRODE CONNECTOR

TECHNICAL AREA

This invention relates to medical diagnostic and therapeutic apparatus employing electrodes and, more particularly, to apparatus for connecting the cables of such medical diagnostic and therapeutic apparatus to the electrodes themselves.

BACKGROUND OF THE INVENTION

The medical profession uses disposable medical electrodes in a variety of ways during the caring of patients. For example, disposable electrodes are used in the performance of such therapeutic and diagnostic functions as patient defibrillation, external cardiac pacing and ECG monitoring. Generally, the disposable electrodes are maintained in contact with the patient's skin by a self-sticking adhesive and are connected to an appropriate medical apparatus by a cable. Appropriate electric signals are transmitted between the electrode and the medical apparatus via the cable. Normally, the cable has a female connector on one end for connecting the cable to the electrode and a male connector on the other end for connecting the cable to the appropriate medical apparatus. The electrodes generally have a male connector (i.e., a post) that can be engaged by the female connector on the end of the cable.

To prevent connecting the wrong cables to the wrong electrodes, such as connecting a defibrillation cable to a pacing electrode, for example, each of the different types of prior art electrodes is equipped with a different shaped post. More specifically, the post on a prior art defibrillation electrode is different than the post on a prior pacing electrode, and both posts are different from the post on a prior art ECG electrode. The female connectors on the different types of cables are matched to the appropriate electrodes and, as a result, are also different from one another. Consequently, in the prior art, an ECG cable can only be connected to an ECG electrode, a defibrillation cable can only be connected to a defibrillation electrode, and a pacing cable can only be connected to a pacing electrode. Thus, by making the male-to-female connections different for each type of electrode, the prior art provides safe patient treatment by preventing the wrong cable from being connected to the wrong electrode. Obviously, such an improper connection could threaten the health of a patient.

The importance of the different types of connections for the different types of electrodes is especially apparent when more than one type of electrode is used on a particular patient. For example, it is a common medical practice to monitor a patient's condition after the patient has been defibrillated. To accomplish this in the prior art, medical personnel must, after defibrillation, remove the defibrillation electrodes from the patient and attach ECG monitoring electrodes to the patient. For the reasons noted above, the defibrillation electrodes are connected to defibrillation cables and the ECG electrodes are connected to ECG cables. If the patient needs to be defibrillated again, such as when the patient's ECG rhythm is absent, the medical personnel must remove the ECG electrodes and attach new defibrillation electrodes to the patient. The ECG electrodes are removed during defibrillation to make room for the defibrillation electrodes and to prevent injury to personnel or damage to equipment that may be connected to the ECG electrodes when the patient is defibrillated. Once the defibrillation and ECG electrodes are removed from a patient, they are normally discarded for such reasons as personal hygiene and to ensure that an electrode that may have been damaged during removal is not reused on a patient. Such a prior art procedure wastes valuable time and is costly, considering the time it takes medical personnel to remove and reattach the electrodes and the cost of the electrodes themselves.

As can be readily appreciated from the foregoing discussion, there has developed a need in the medical profession for a discriminating medical electrode connector, whereby a disposable defibrillation electrode can be used, at separate times, for defibrillation and ECG monitoring of the same patient. Such a discriminating connector should also offer patient safety be preventing the connection of a defibrillation cable to an ECG monitoring electrode which might permit an inadvertent defibrillation of the patient to be attempted through use of the ECG monitoring electrode. The present invention provides these results.

SUMMARY OF THE INVENTION

In accordance with this invention, a discriminating connector is provided for connecting a defibrillation electrode, but not an ECG monitoring electrode, to a cable, wherein the defibrillation electrode has a conducting post located a first distance from an outer edge thereof, and the ECG monitoring electrode has a conducting post substantially identical to the conducting post of the defibrillation electrode and located a second distance from an outer edge of the ECG monitoring electrode. In electrodes of this type, the second distance is substantially greater than the first distance.

The connector comprises:

a housing means having an opening that is configured to permit a medical electrode having a conducting post to be inserted edge first therein. The housing means includes an upper member having sides and first and second ends, a lower member having sides and first and second ends, wherein the lower member is substantially parallel to and spaced apart from the upper member, and a connecting member located between the first and second ends of the upper and lower members and connecting the upper and lower members. The opening is defined by an upper wall formed by the upper member between the first end of the upper member and the connecting member, a lower wall formed by the lower member between the first end of the lower member and the connecting member, and a back wall formed by the connecting member; and, a conductive receiving means disposed within the opening of the housing means for receiving the conducting post of the medical electrode, wherein the housing means is constructed to permit the insertion of the medical electrode into the opening to a depth which is at least equal to that required for the conductive receiving means to receive the conducting post of the defibrillation electrode, but which is less than that required to receive the conducting post of the ECG monitoring electrode.

DETAILED DESCRIPTION OF THE PREFERRED EMBODIMENT

In a broad sense, the present invention allows one type of disposable electrode to be used for different purposes at different times on the same patient. More particularly and in accordance with the preferred embodiment of the invention, a disposable defibrillation electrode can be connected to a defibrillation cable or to an ECG cable. When connected to the defibrillation cable, the defibrillation electrode performs a defibrillation function and when connected to the ECG cable, the defibrillation electrode performs an ECG monitoring function. As will become better understood from the following discussion, a discriminating connector attached to one end of the defibrillation cable permits connecting the defibrillation cable to the defibrillation electrode, but prevents connecting the defibrillation cable to any other type of electrode, such as an ECG electrode. As will also become better understood from the following discussion, a prior art ECG cable connector can be connected to the defibrillation electrode. A brief review of the prior art is presented next, followed by a detailed discussion of the present invention.

Figure 1A:
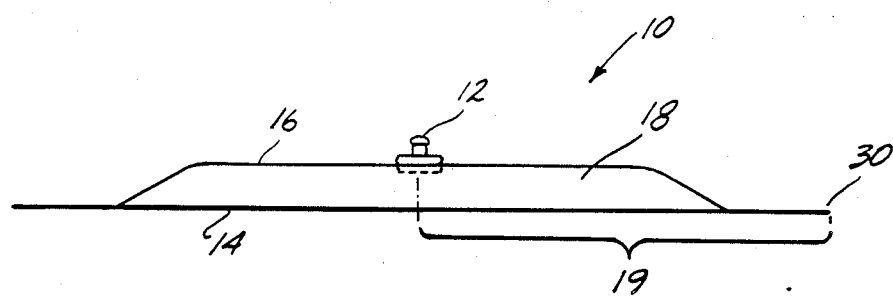
FIG. 1A is a schematic side view of a typical disposable ECG monitoring electrode used in the prior art.

FIG. 1A illustrates a typical disposable ECG monitoring electrode 10 used in the prior art. The ECG electrode 10 comprises: a conducting post 12; a skin-contacting surface 14; a backing layer 16; and a conductive gel 18. The conductive gel 18 is contained within a reservoir formed by the backing layer 16. The skin-contacting surface 14 is formed by a surface of the gel 18 that is opposite the backing layer 16. The conducting post 12 is attached to the electrode 10 so that a first end of the conducting post 12 protrudes from the backing layer 16 and a second end of the conducting post 12 is in contact with the gel 18. The conducting post 12 is located at the center of the ECG electrode 10. A longitudinal centerline of the conducting post 12 is generally normal to the skin-contacting surface 14 and is located a distance 19 from an outer edge 30 of the electrode 10.

Several features of the ECG electrode 10 are illustrated in FIG. 1A and discussed above. So as to permit a better understanding of the prior art, however, as will become better understood from the following discussion, only the conducting post 12 and distance 19 are of importance to the present invention.

Figure 1B:
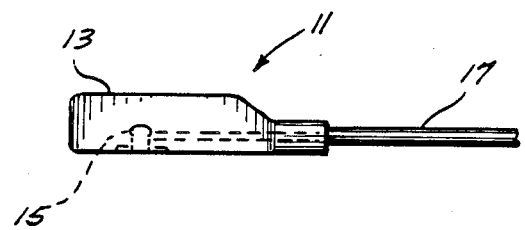
FIG. 1B is a sectional view of a typical ECG cable connector suitable for use with the prior art ECG electrode illustrated in FIG. 1A.

FIG. 1B illustrates a typical prior art connector 11 that can be used with the prior art ECG monitoring electrode 10 discussed above. The connector 11 is attached to one end of an ECG cable 17. The connector 11 comprises a housing 13 and a conductive female receptacle 15. The housing 13 is made of a suitable insulating material, such as a nonconductive plastic, for example, The conductive female receptacle 15 is contained within the housing 13. The ECG cable 17 enters the housing 13 and is attached to the female receptacle 15 in a conventional manner, such as with a solder joint. The other end of the cable 17 (not shown) can be connected to an ECG apparatus capable of monitoring patient ECG signals.

The female receptacle 15 is appropriately shaped so that it may engage the conducting post 12 on the ECG electrode 10. This relationship is further illustrated by comparing FIGS. 1A and 1B. When the connector 11 is coupled to the ECG electrode 10 so that the post 12 is received by the receptacle 15, the electrode 10, connector 11 and cable 17 form an ECG lead that is capable of supplying patient ECG signals to an ECG monitoring apparatus.

Figure 2A:
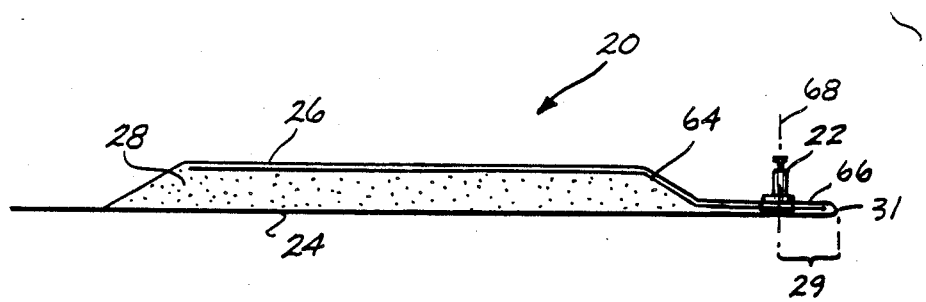
FIG. 2A is a schematic side view of a typical disposable defibrillation electrode used in the prior art.

Turning next to yet another example, FIG. 1A illustrates a typical disposable defibrillation electrode 20 used in the prior art. The defibrillation electrode 20 comprises: a conducting post 22; a skin-contacting surface 24; a backing layer 26; a conductive gel 28; a conducting plate 64; and, a peripheral portion 66. The gel 28 is contained within a reservoir formed by the backing layer 26. The conducting plate 64 is sandwiched between the backing layer 26 and the gel 28. The skin-contacting surface 24 is partially formed by a surface of the gel 28 that is opposite the plate 64. The peripheral portion 66 is an outer annular portion of the electrode 20 that includes a part of the backing layer 26 and forms part of the skin contacting surface 24. The plate 64 extends into the peripheral portion 66. The conducting post 22 is connected to the defibrillation electrode 20 so that a first end of the conducting post 22 protrudes through peripheral portion 66 of the backing layer 26. A second end of the conducting post 22 is in contact with the conducting plate 64. A longitudinal centerline 68 of the conducting post 22 is located a distance 29 from an outer edge 31 of the defibrillation electrode 20. As with the ECG electrode 10, discussed above, various features of the prior art defibrillation electrode 20 are illustrated in FIG. 2A and discussed above so as to permit a better understanding the prior art; however, only the conducting post 22 is of particular interest with regard to the present invention.

Figure 2B:
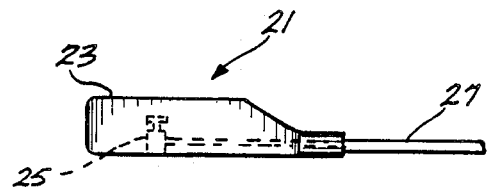
FIG. 2B is a schematic side view of a typical defibrillation cable connector suitable for use with the prior art defibrillation electrode illustrated in FIG. 2A.

FIG. 2B illustrates a typical prior art connector 21 that is used with the prior art defibrillation electrode 20, discussed above. The connector 21 is attached to one end of a defibrillation cable 27. The connector 21 comprises: a housing 23 made of a suitable insulating material such as a nonconductive plastic; and, a conductive female receptacle 25 contained within the housing 23. The defibrillation cable 27 enters the housing 23 and is attached to the female receptacle 25 in a conventional manner, such as with a solder joint. The other end of the cable 27 (not shown) can be connected to a defibrillation apparatus capable of supplying defibrillation signals to a patient.

The female receptacle 25 is appropriately shaped so that it may engage the conducting post 22 on the defibrillation electrode 20. This relationship is further illustrated by comparing FIGS. 2A and 2B. When the connector 21 is coupled to the defibrillation electrode 20, so that the post 22 is received by the receptacle 25, the electrode 20, the connector 21 and the cable 27 form a defibrillation lead that is capable of delivering defibrillation signals from a defibrillation apparatus to a patient.

As noted above, the conducting post 12 attached to the prior art ECG electrode 10 can be engaged only by the receptacle 15 in the prior art ECG connector 11. Likewise the conducting post 22 attached to the prior art defibrillation electrode 20 can be engaged only by the female receptacle 25 in the prior art defibrillation connector 21. This exclusivity between electrodes 10 and 20 and connectors 11 and 21 is accomplished in the prior art by making the shape of the ECG conducting post 12 substantially different from the shape of the defibrillation conducting post 22. Consequently, the shape of the ECG receptacle 15 is substantially different from the shape of the defibrillation receptacle 25. As a result, the ECG conducting post 12 cannot be engaged by the receptacle 25 in the defibrillation connector 21 and the defibrillation conducting post 22 cannot be engaged by the receptacle 15 in the ECG connector 11. This relationship is graphically illustrated in FIGS. 1A, 1B, 2A, and 2B. The ECG conducting post 12 has a conventional button shape suitable for use with a conventional snap connector. Contrariwise, the defibrillation conducting post 22 has a cylindrical shape with a narrow neck near the first end (i.e., the end protruding from the backing layer 26 of the electrode 20) that is not suitable for use with a conventional snap connector.

Figure 3:
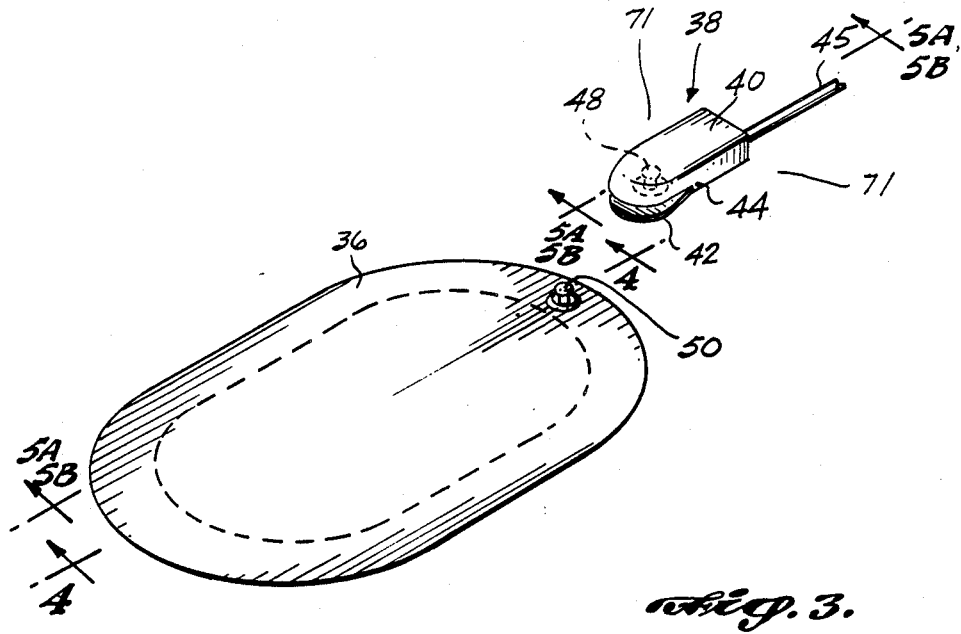
FIG. 3 is an isometric view of a preferred embodiment of a discriminating connector formed in accordance with the present invention and a defibrillation electrode suitable for use with the discriminating connector.

Turning next to the present invention, FIG. 3 illustrates a preferred embodiment of a discriminating connector 38 formed in accordance with the invention and a defibrillation electrode 36 that is suitable for use with the discriminating connector 38. The defibrillation electrode 36 includes a conducting member, such as a conducting post 50, that can be engaged by a receiving member, such as a mating receptacle 48, contained within the discriminating connector 38. As will be better understood from the following discussion, the defibrillation electrode 36 may be connected to a defibrillation apparatus via the discriminating connector 38 or to an ECG monitoring apparatus via the ECG connector 11, but the discriminating connector 38 can only be connected to the defibrillation electrode 36. As a result, a patient attached to the defibrillation electrode 36 can be defibrillated or have his or her ECG signals monitored using the same defibrillation electrode 36, however, the patient cannot be accidentally defibrillation through an ECG monitoring electrode because the discriminating connector 38 cannot be connected to an ECG monitoring electrode.

Figure 4:
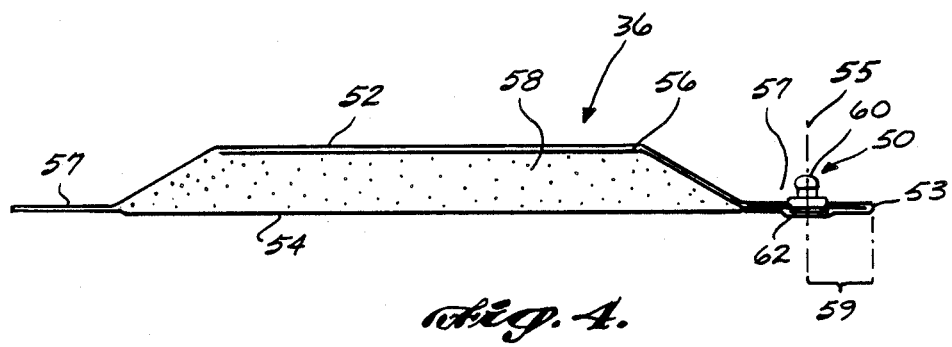
FIG. 4 is a sectional view of the defibrillation electrode illustrated in FIG. 3.

FIG. 4 is a sectional view of the defibrillation electrode 36 which illustrates a principal distinction between the defibrillation electrode 36 and the prior art defibrillation electrode 20 discussed above and illustrated in FIG. 2A. As will become better understood from the following discussion, the shape of the conducting post 50 is different than the shape of the prior art conducting post 22. In accordance with the preferred embodiment of the invention the conducting post 50 has the same shape as the conducting post 12 used with prior art ECG electrode 10 discussed above and illustrated in FIG. 1A, namely, a button shape suitable for use with a conventional snap connector. The defibrillation electrode 36 comprises: the conducting post 50; a backing layer 52; a skin-contacting surface 54; a conductive plate 56; a conductive gel 58; and a peripheral portion 57. The gel 58 is contained in a reservoir formed by the backing layer 52. The conductive plate 56 is preferably sandwiched between, an in intimate contact with, the backing layer 52 and the gel 58. The skin-contacting surface 54 is partially formed by a surface of the gel 58 that is opposite the plate 56. The peripheral portion 57 is an outer annular portion of the electrode 36 that includes a part of the backing layer 52 and forms a part of the skin-contacting surface 54. The plate 56 extends into the peripheral portion 57. The post 50 is attached to the peripheral portion 57. A first, i.e., connector, end 60 of the post 50 extends normally from the backing layer 52 of the periphery portion 57 opposite the skin-contacting surface 54. A second, i.e., electrode, end 62 of the post 50 is contained within peripheral portion 57 and is in intimate contact with the conductive plate 56. As a result, electrical continuity is provided between the connector end 60 of the post 50, the conductive plate 56 and the gel 58. A longitudinal centerline 55 of the post 50 is located a distance 59 from an outer edge 53 of the electrode 36.

Figure 5B:
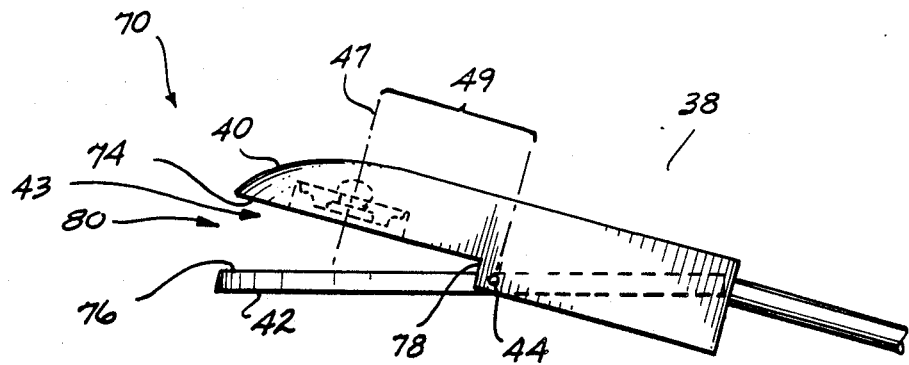
FIGS. 5A and B are sectional views of the discriminating connector illustrated in FIG. 3.
Figure 5A:
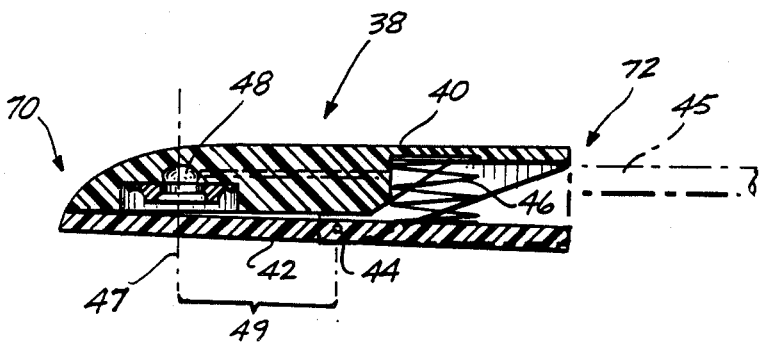

FIG. 5A illustrates, in section, the connector 38 in a closed position. The connector 38 comprises: an upper member 40; a lower member 42; a biasing spring 46; and, a conductive receiving means, such as a mating receptacle 48. The upper members 40 and 42 have first, or post, ends 70 and second, or cable, ends 72 opposite the post ends 70 and sides 71 (FIG. 3). The upper and lower members 40 and 42 are joined by a pivot 44 whose pivotal axis is substantially normal to the sides 71 of the upper and lower members 40 and 42. The pivot 44 is located between ends 70 and 72 of the upper and lower members 40 and 42 and coplanar with the lower member 42. The biasing spring 46 is connected between the upper and lower members 40 and 42 between the pivot 44 and the cable ends 72 of the upper and lower members 40 and 42. The spring 46 biases the cable ends 72 of the upper and lower members 40 and 42 away from one another, while biasing the post ends 70 of the upper and lower members 40 and 42 toward one another. The mating receptacle 48 is displaced within the upper member 40 and located between the pivot 44 and the post end 70 of the upper member 40. A longitudinal centerline 49 of the mating receptacle 48 is located a distance 49 from the pivot 44. The mating receptacle 48 is preferably a female receptacle suitably shaped so as to engage the male end (i.e., the button) of a conventional snap connector, such as the conducting post 50 attached to the defibrillation electrode 36, discussed above. A defibrillation cable 45 enters the cable end 72 of the upper member 40. The cable 45 passes through the upper member 40 and is attached to the mating receptacle 48 in a conventional manner, such as with a solder joint.

FIG. 5B illustrates the discriminating connector 38 in an open position (i.e., with the biasing spring compressed). In the open position, the upper and lower members 40 and 42 and the pivot 44 form an opening 43. More specifically, an upper wall 74 of the opening 43 is formed by the upper member between the first end 70 and the pivot 44, a lower wall 76 of the opening 43 is formed by the lower member 42 between the first end 70 and the pivot 44. A back wall 78 is substantially formed by the pivot 44. As will be better understood from the following discussion, a front wall 80 is opposite the back wall 78 and is open when the first ends 70 of the upper and lower members 40 and 42 are spaced apart. The depth of the opening is defined as the distance 49 between the centerline 47 of the mating receptacle 48 and the pivot 44.

Upper and lower members 40 and 42 are made of a suitable insulating material, such as a nonconductive plastic. Members 40 and 42 are sufficiently rigid, so that by "pinching" the cable ends 72 together and compressing the spring 46, the post ends 70 of the members 40 and 42 are forced apart so as to open the discriminating connector 38. By releasing the cable ends 72, the previously compressed spring 46 is allowed to return to its uncompressed state, thereby forcing the cable ends 72 of members 40 and 42 apart and causing the post ends 70 of the members 40 and 42 to move toward one another so as to close the discriminating connector 38.

Figure 6:
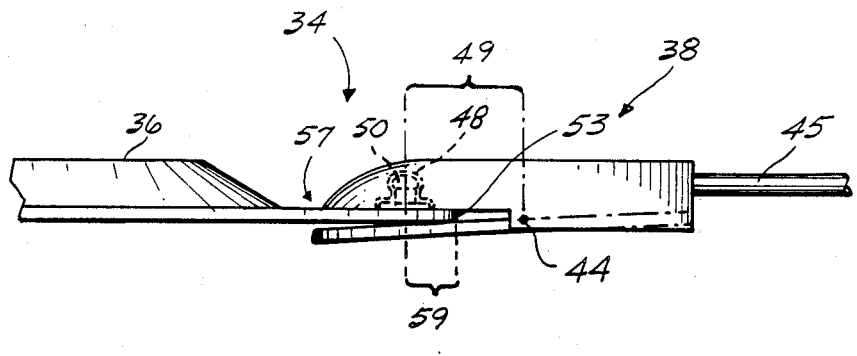
FIG. 6 is a schematic side view illustrating how the discriminating connector depicted in FIG. 5A is connected to the defibrillation electrode depicted in FIG. 4.

FIG. 6 illustrates the connection of the discriminating connector 38 to the defibrillation electrode 36. To make the connection, the cable ends 72 of members 40 and 42 are pressed towards one another (i.e., "pinched") so as to open the connector 38 in the manner described above. The discriminating connector 38 is proximally positioned with the electrode 36 such that the peripheral portion 34 of the defibrillation electrode 36 is inserted edgewise into the opening 43. Next, the centerline 55 of the post 50 and the centerline 49 of the receptacle 48 are aligned so that when the cable ends 72 of members 40 and 42 are released, the post ends 70 of members 40 and 42 move towards one another, thereby causing the receptacle 48 to engage the conducting post 50. The receptacle 48 engages and makes electrical contact with the post 50, in part, because the distance 59 from the post 50 to the outer edge 53 of the electrode 36 is less than or equal to the distance 49 between the receptacle 48 and the pivot 44 of the connector 38, as illustrated in FIG. 6. As a result, when the above connection is made, defibrillation signals can be supplied to a patient via a defibrillation lead formed by the cable 45, the discriminating connector 38 and the defibrillation electrode 36.

Figure 7:
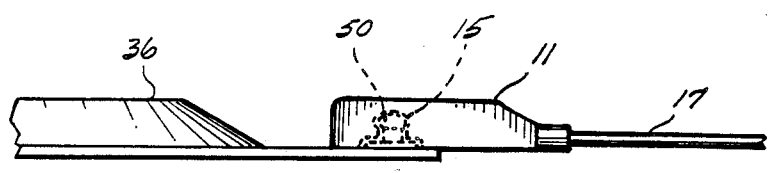
FIG. 7 is a schematic side view illustrating how the prior art ECG cable connector depicted in FIG. 1B is connected to the defibrillation electrode depicted in FIG. 4; and, FIG. 8 is a schematic side view illustrating why the discriminating connector depicted in FIG. 5 cannot be connected to the prior art ECG monitoring electrode depicted in FIG. 1A.

FIG. 7 illustrates how the prior art ECG connector 11 can be connected to the defibrillation electrode 36. The prior art ECG connector 11 may be attached to the defibrillation electrode 36 by aligning the female receptacle 15 of the connector 11 with the post 50 and pressing the connector 11 onto the post 50. Since, as noted above, the post 50 of the present invention is the same shape as the post 12 of the prior art ECG electrodes, and the female receptacle 15 is the same shape as the mating receptacle 48, the post 50 may be engaged by the female receptacle 15. Thus, electrical contact is made between the prior art ECG connector 11 and the defibrillation electrode 36. When such a connection is made, patient ECG signals can be applied to a monitoring apparatus via an ECG lead formed by the cable 17, the connector 17 and the defibrillation electrode 36.

Figure 8:
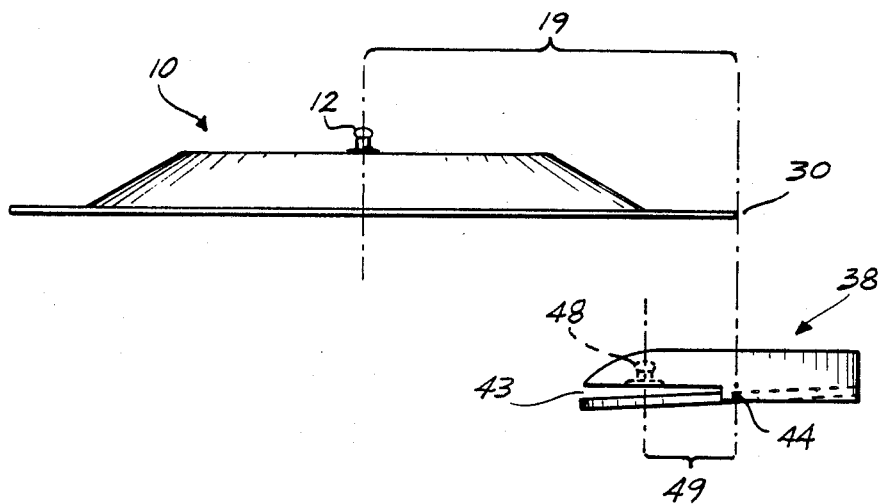

As noted above and illustrated in FIG. 8, the discriminating connector 38 cannot be connected to a prior art ECG monitoring electrode 10. The discriminating connector 38 is prevented from engaging the conducting post 12 of the prior art ECG electrode 10 because the distance 19 between the outer edge 30 and post 12 of the ECG electrode 10 exceeds the distance 49 between the receptacle 48 and the pivot 44 of the discriminating connector 38. As a result, the prior art ECG electrode 10 cannot be inserted edgewise into the opening 43 of the discriminating connector 38 a sufficient distance to permit the conducting post 12 to be engaged by the mating receptacle 48. Thus, electrical contact cannot be made between the prior art electrode 10 and the discriminating connector 38 of the present invention. It is such in a manner that the present invention provides patient safety by assuring that the defibrillation signals cannot be applied to the patient via an inadvertent connection between the discriminating connector 38 and the ECG electrode 10.

As can be readily appreciated from the foregoing description, the present invention provides a discriminating connector 36 that ensures patient safety while reducing the labor and material costs associated with changing disposable electrodes that are attached to the patient by reducing the number of disposable electrodes which must be used on a patient. While a preferred embodiment of the invention has been illustrated and described herein, it is to be understood that within the scope of the appended claims, various changes can be made. For example, the post 50 can have any shape as long as it has the same shape as the post 12 on the prior art ECG monitoring electrode 10. Likewise, other forms of the discriminating connector 38 may work equally well, such as a C-clamp type of connector, for example, as long as the relationships between the critical distances (i.e., distances 19, 49 and 59) are maintained. Further, the discriminating feature of the invention may be adapted to other medical electrodes, such as external pacing electrodes, for example. Hence, the invention can be practiced otherwise than as specifically described herein.

The embodiments of the invention in which an exclusive property or privilege is claimed are defined as follows:

1. A discriminating connector for connecting a defibrillation electrode but not an ECG monitoring electrode to a cable, the defibrillation electrode having a conducting post located a first distance from an outer edge of the defibrillation electrode and the ECG monitoring electrode having a conducting post substantially identical to the conducting post of the defibrillation electrode located a second distance from an outer edge of the ECG monitoring electrode, the second distance being substantially greater than the first distance, wherein the discriminating connector comprises:
   (a) housing means having an opening that is configured to permit a medical electrode having a conducting post to be inserted edge first therein, wherein said housing means includes an upper member having sides and first and second ends, a lower member having sides and first and second ends, wherein said lower member is substantially parallel to and spaced apart from said upper member, and a connecting member located between said first and second ends of said upper and lower members and connecting said upper and lower members, and wherein said opening is defined by an upper wall formed by said upper member between said first end of said upper member and said connecting member, a lower wall formed by said lower member between said first end of said lower member and said connecting member, and a backwall formed by said connecting member; and,
   (b) conductive receiving means disposed within said opening of said housing means for receiving said conducting post of said medical electrode, wherein said housing means is constructed to permit the insertion of said medical electrode into said opening to a depth which is at least equal to that required for said conductive receiving means to receive the conducting post of the defibrillation electrode but which is less than that required to receive the conducting post of the ECG monitoring electrode.

2. The discriminating connector claimed in claim 1, wherein said conductive receiving means is a mating receptacle constructed to mate with said conducting post, wherein said mating receptacle is disposed within said upper member.

3. The discriminating connector claimed in claim 2, wherein said conducting post and said mating receptacle form a snap connector.

4. The discriminating connector claimed in claim 1, wherein said connecting member comprises a pivot having a pivotal axis that is substantially parallel with said upper and lower members and substantially normal to said sides of said upper and lower members.

5. The discriminating connector claimed in claim 4, wherein said conductive receiving means is a mating receptacle constructed to mate with said conducting post, wherein said mating receptacle is disposed within said upper member.

6. The discriminating connector claimed in claim 5, wherein said conducting post and said mating receptacle form a snap connector.

7. The discriminating connector claimed in claim 4, wherein said discriminating connector further comprises a spring, said spring biasing said first ends of said upper and lower members together and biasing said second ends of said upper and lower members apart.

8. The discriminating connector claimed in claim 7, wherein said conductive receiving means is a mating receptacle constructed to mate with said conducting post, wherein said mating receptacle is disposed within said upper member.

9. The discriminating connector claimed in claim 8, wherein said conducting post and said mating receptacle form a snap connector.

10. The discriminating connector claimed in claim 9, wherein said upper and lower members are substantially nonconductive.

11. The discriminating connector claimed in claim 10, wherein said upper and lower members are formed of a substantially rigid material.

* * * * *

UNITED STATES PATENT AND TRADEMARK OFFICE
CERTIFICATE OF CORRECTION

PATENT NO. : 4,915,656
DATED : April 10, 1990
INVENTOR(S) : Clifton A. Alferness It is certified that error appears in the above-identified patent and that said Letters Patent is hereby corrected as shown below:

```
Column 2, line 17:   "be" should be --by--
Column 4, line 30:   "FIG. 1A" should be --FIG. 2A--
Column 5, line 55:   "defibrillation" should be --defibrillated--
Column 7, line 59:   "connector 17" should be --connector 11--
Column 8, line 7:    "such in" should be --in such--
```

Signed and Sealed this

Thirtieth Day of July, 1991

Attest:

HARRY F. MANBECK, JR.

*Attesting Officer*  *Commissioner of Patents and Trademarks*